United States Patent [19]

Yasuda et al.

[11] 4,099,922

[45] Jul. 11, 1978

[54] GAS COMPONENT DETECTION APPARATUS

[75] Inventors: Eturo Yasuda; Susumu Sato; Yoshihiro Segawa; Tadashi Hattori, all of Okazaki; Keiji Aoki, Susono, all of Japan

[73] Assignees: Nippon Soken, Inc., Nishio; Toyota Jidosha Kogyo Kabushiki Kaisha, Toyota, both of Japan

[21] Appl. No.: 751,956

[22] Filed: Dec. 17, 1976

[30] Foreign Application Priority Data

Dec. 23, 1975 [JP] Japan .................. 50-154334

[51] Int. Cl.² ........................... G01N 27/16
[52] U.S. Cl. ............................... 23/254 E
[58] Field of Search .......... 23/254 E; 340/237 R; 338/34

[56] References Cited

U.S. PATENT DOCUMENTS

| 3,479,257 | 11/1969 | Shaver | 23/254 E X |
| 3,695,848 | 10/1972 | Taguchi | 23/254 E |
| 3,901,067 | 8/1975 | Boardman | 23/254 E X |

*Primary Examiner*—Robert M. Reese
*Attorney, Agent, or Firm*—Cushman, Darby & Cushman

[57] ABSTRACT

A gas component detection apparatus for detecting gaseous components of exhaust gases from a combustion device. There is provided a gas component detecting element composed of semiconductive metal oxides and having its outer surface partly exposed to the exhaust gases. A catalyst layer is carried on the larger part of the latter outer surface of the detecting element. A pair of electrodes are provided for sensing the electric resistance exhibited at the portion of the detecting element which carries the catalyst layer. Also another electrode is provided for cooperating with one of the above pair of electrodes to detect the electric resistance exhibited at the portion of the detecting element which does not carry the catalyst layer. The former portion of the detecting element exhibits variable electric resistances resulting from concentrations of the gaseous components and the temperatures of the exhaust gases, while the latter portion thereof exhibits variable electric resistances related mainly upon the temperatures of the exhaust gases. Consequently, an output signal reflecting substantially only the gaseous components of the exhaust gases is produced by offsetting both of the electric resistances separately sensed utilizing a suitable electric circuit.

9 Claims, 14 Drawing Figures

GAS COMPONENT DETECTION APPARATUS

BACKGROUND OF THE INVENTION

The present invention relates to a gas component detection apparatus of the type described in the applicant's earlier U.S. application, Ser. No. 662,956, and more particularly to a gas component detection apparatus for detecting the variation in concentrations of gaseous components such as oxygen ($O_2$), carbon monoxide (CO) and hydrocarbon (HC) of exhaust gases from combustion devices such as an internal combustion engine.

Gas component detection apparatuses have been widely used in many industrial fields. Lately, as a countermeasure to cope with the problem of exhaust gases from an internal combustion engine, gas component detection apparatuses have been employed for determining the air-fuel ratio of an air-fuel mixture supplied to the internal combustion engine.

In the case where a catalyst is utilized for purifying exhaust gases from an internal combustion engine, the catalyst cannot exhibit maximum properties unless the air-fuel ratio of an air-fuel mixture is maintained constantly at a proper value. However, in an ordinary internal combustion engine equipped with a conventional carburetor or a fuel injection apparatus, the air-fuel ratio is actually inevitably subjected to a large variation even when the ratio of injected fuel to intake air is set to be constant. Consequently, in order to maintain constantly a proper air-fuel ratio, it is necessary to detect with the use of gas detection apparatuses air-fuel ratio prior to the burning of the air-fuel mixture and feed back signal corresponding to the detected value to the carburetor or the injection apparatus, thereby controlling the air-fuel ratio of the air-fuel mixture supplied to the engine.

Gas component detection apparatuses are constructed to determine the air-fuel ratio based on the fact that variation in concentrations of gaseous components of the exhaust gases is closely related to variation of the air-fuel ratio of the air-fuel mixture. In this connection, consideration has to be given to the fact that the temperature of the exhaust gases, as well as the concentrations of the gaseous components thereof, will vary abruptly and remarkably. It is thus desirable that the gas component detection apparatuses be operable with high accuracy notwithstanding such prominent variables.

Heretofore, a gas component detection apparatus has been known which employs transition metal oxides. Such a detection apparatus is mounted for example in an exhaust pipe of an internal combustion engine with the transition metal oxides exposed to the exhaust gases, and the electric resistance variation thereof is detected to determine the air-fuel ratio. However, the electric resistances exhibited by the transition metal oxides vary depending upon not only the concentrations of the gaseous components of the exhaust gases, but also the temperatures thereof. Therefore, in order to determine with high accuracy the air-fuel ratio and thus to effect proper control of the air-fuel ratio, it is necessary to make a temperature compensation, i.e., to compensate for the electric resistance variation of the transition metal oxides due to the temperature of the exhaust gases.

SUMMARY OF THE INVENTION

It is therefore an object of the present invention to provide a gas component detection apparatus which can detect with high accuracy gaseous components of exhaust gases, without being influenced by the temperature of the exhaust gases.

According to the present invention, there is provided a gas component detection apparatus for detecting gaseous components of exhaust gases from a combustion device comprising a gas component detecting element having a surface partially exposed to the exhaust gases from the combustion device and exhibiting variable electric resistances according to both the gaseous components and temperatures of the exhaust gases; a catalyst carried on a larger part of the surface of the detecting element exposed to the exhaust gases for promoting an oxidation reaction of the gaseous components of the exhaust gases; a pair of electrodes inserted into the detecting element in a manner so as not to be short-circuited through the catalyst and having their outer ends disposed adjacent the catalyst for sensing an abrupt change in electric resistance exhibited at that portion of the detecting element near the catalyst as a result of the gaseous components and the temperature of the exhaust gases; and another electrode disposed in the detecting element in spaced relationship from the catalyst for detecting, in association with one of the aforesaid pair of electrodes, a change in electric resistance resulting mainly from the temperatures of the exhaust gases at that portion of the detecting element substantially spaced from the catalyst.

The gas component detection apparatus of the present invention is preferably used with an internal combustion engine to determine whether the air-fuel ratio of the air-fuel mixture supplied thereinto is larger or smaller than the stoichiometrical air-fuel ratio, thereby controlling the air-fuel ratio of the air-fuel mixture supplied into the engine at the stoichiometrical air-fuel ratio.

Preferably, the gas component detecting element is composed of a sintered mass of semiconductive metal oxides, and a catalyst covered with an electrically insulative porous ceramic film.

The above objects as well as novel features and advantages of the invention will become more apparant from the following description when read in conjunction with the accompanying drawings.

DETAILED DESCRIPTION OF THE INVENTION

Figure 1:
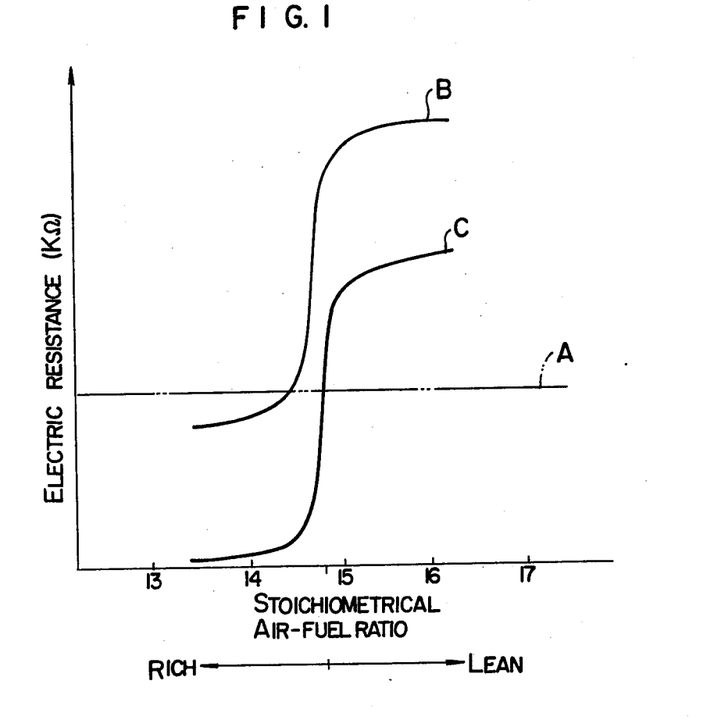
FIG. 1 graphically illustrates a relationship between the air-fuel ratio of the air-fuel mixture and an electric resistance of transition metal oxides exposed to exhaust gases.

The invention now will be described in detail with reference to the drawings. Referring first to FIG. 1, there is graphically shown a relationship between an air-fuel ratio of an air-fuel mixture and an electric resistance of transition metal oxides exposed to the exhaust gas. A characteristic curve B represents the relation obtained when the exhaust gas is at a temperature of 350° C, while characteristic curve C represents the relation obtained when the exhaust gas is at 850° C. These curves clearly show that the electric resistance exhibited by the transition metal oxides varies depending upon not only the concentrations of gaseous components of the air-fuel mixture, but also the temperature of the exhaust gas.

In the case where an air-fuel ratio of an air-fuel mixture is determined by employing transition metal oxides, a differential operational amplifier is used which has a non-inverted input terminal to which a reference voltage set by reference resistors is applied and an inverted input terminal to which a voltage set by the electric resistance of the transition metal oxides is applied. The amplifier compares the voltages applied to both its input terminals and produces a corresponding output signal. The latter signal can be utilized to control the air-fuel ratio of the air-fuel mixture supplied to a combustion device. However, in order to effect proper control of the air-fuel ratio by employing the transition metal oxides, it is necessary to compensate the electric resistance variation of the transition metal oxides due to temperature variation of the exhaust gas. As will be understood from FIG. 1, in the case where the reference voltage is set to control the air-fuel ratio to the stoichiometrical one (such reference voltage being represented by a phantom line A in FIG. 1 in terms of electric resistance), such control can be effected when the temperature of the exhaust gas is 850° C. However, when the exhaust gas is at 350° C, the air-fuel ratio is smaller than the stoichiometrical one, which makes precise control of the air-fuel ratio impossible.

Figure 2:
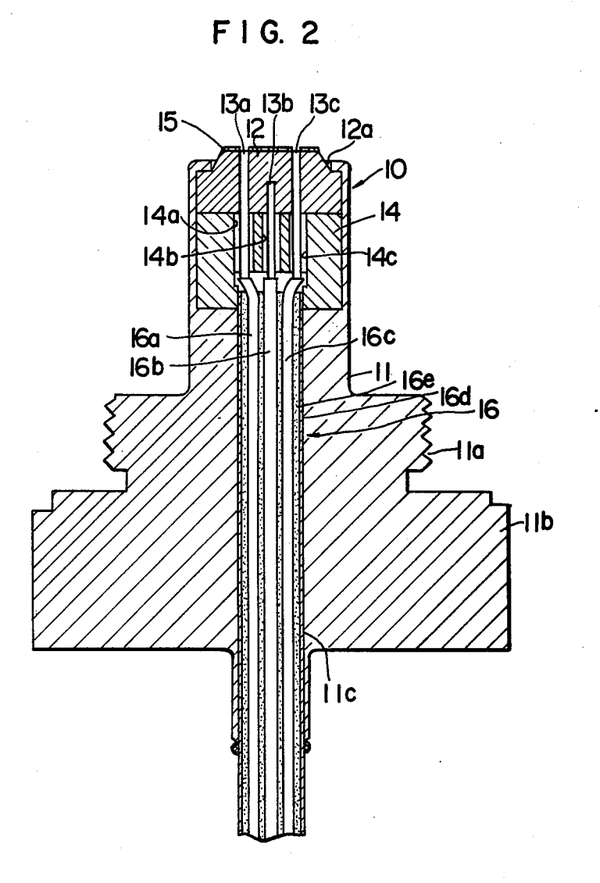
FIG. 2 is a vertical sectional view of a first embodiment of a gas component detection apparatus according to the present invention, with the lower portion of a sheathed cable cut away.
Figure 3:
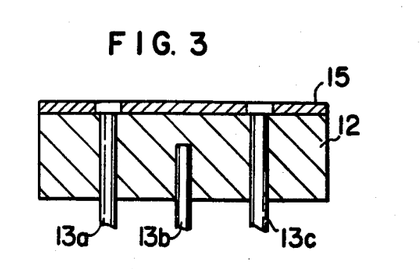
FIG. 3 is an enlarged sectional view showing an essential part of the detection apparatus of FIG. 2.
Figure 4:
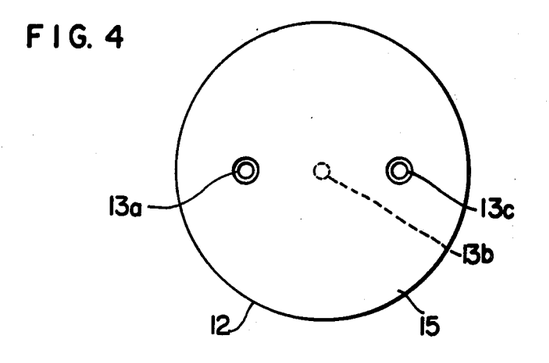
FIG. 4 is a plan view of the part of the detection apparatus shown in FIG. 3.

FIGS. 2 to 4 show the structure of a first embodiment of a gas component detection apparatus 10 in accordance with the present invention. Referring to these figures, the detection apparatus 10 shown comprises a housing 11 made of heat-resistant and corrosion-resistant metal material. The housing 11 has a threaded portion 11a and a tightening portion 11b by which the housing 11 may be mounted on an exhaust pipe of an internal combustion engine. A disc-like gas component detecting element 12 made of a sintered mass of semiconductive metal oxides has a tapered upper peripheral edge 12a. The detecting element 12 may be made of transition metal oxides such as titanium oxide ($TiO_2$), nickel oxide (NiO), cobalt oxide (CoO), manganese oxide (MnO), zinc oxide (ZnO), copper oxide (CuO) and niobium oxide ($Nb_2O_5$), and tin oxide ($SnO_2$). In the detecting element 12 are inserted and embedded in spaced relationship the upper portions of three bar-like electrodes 13a, 13b and 13c each made of heat-resistant and corrosion-resistant metal materials such as platinum (Pt) and gold (Au). A spacer 14 made of an electrically insulative ceramic material is disposed below the detecting element 12. The spacer 14 has three apertures 14a, 14b and 14c into which the lower portions of the electrodes 13a, 13b and 13c, respectively, are inserted. The three electrodes 13a, 13b and 13c are prevented from being short-circuited by the spacer 14. The spacer and the detecting element 12 are received in the housing 11 and are fixed in position by the upper end of the housing 11 being inwardly bent. The detecting element 12 carries on its top or outer surface a catalyst layer 15 composed of palladium (Pd), rhodium (Rh) or the like which is effective to oxidize gaseous components of exhaust gases. The catalyst layer 15 is applied to the outer surface of the detecting element 12, for example, by impregnating the detecting element 12 in chloroplatinate ($H_2PtCl_4.6H_2O$), deoxidizing same in a hydrogen current and then sintering it.

Two of the three electrodes, i.e., the electrodes 13a and 13c have their outer end surfaces exposed at the top surface of the detecting element 12, while the other electrode 13b has its outer end located inside the detecting element 12. The catalyst layer 15 is carried on the top surface of the detecting element 12 as described. However, it is not carried by the outer end surfaces of the electrodes 13a and 13c. Thus, the electrodes 13a and 13c are prevented from being short-circuited through the catalyst layer 15. The housing 11 is formed with a longitudinal aperture 11c of large diameter, and into this aperture 11c is inserted a sheathed cable 16 consisting: of a protecting tube 16d made of heat-resistant metal material; lead wires 16a, 16b and 16c within the tube and made of metal materials having high heat resistance as well as high electrical conductivity; and heat resistant and electrically insulating powdery materials filling the balance of the protecting tube 16d. The top ends of the respective lead wires 16a, 16b and 16c are connected by welding or the like to the bottom ends of the respective electrodes 13a, 13b and 13c. Additionally, the sheathed cable 16 is secured to the bottom end of the housing 11 in a manner for example, such as by plasma welding.

Figure 5:
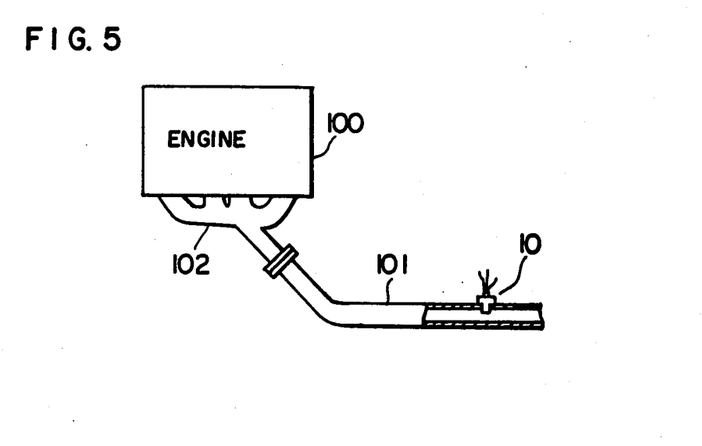
FIG. 5 is a schematic diagram showing, partly in cross-section, a gas component detection apparatus mounted in an exhaust pipe of an internal combustion engine.

Referring next to FIG. 5, the gas component detection apparatus 10 is mounted in an exhasut pipe 101 of an ordinary internal combustion engine 100 using gasoline as a fuel, in such a manner that the detecting element 12 is adapted to be exposed to the exhaust gases. It will be understood that the detection apparatus 10 also may be mounted in that portion of an exhaust manifold 102 at which a plurality of branched pipes of the manifold 102 come together. As is well-known, the exhaust gases are composed of gaseous components such as oxygen ($O_2$), nitrogen oxides (NOx), carbon monoxide (CO), hydrocarbon (HC) and hydrogen ($H_2$), and the concentration of each of these gaseous components varies depending upon the air-fuel ratio of the air-fuel mixture prior to burning. The detecting element 12 is influenced or acted upon mainly by the concentrations or partial pressures of oxygen ($O_2$), carbon monoxide (CO) and hydrocarbon (HC), and exhibits variable electric resistance values according to the variation in the overall exhaust gas condition brought about by variations in the partial pressures of these individual gaseous components. The detecting element 12 is also influenced by the temperature of the exhaust gas, and exhibits variable electric resistance values according to this temperature. On the surface of the detecting element 12 exposed to the exhaust gases is carried the catalyst layer 15 as described. Therefore, when the exhaust gases contact the catalyst layer 15, the following typical reactions will take place under the action of the catalyst layer 15.

(In these formulae, X, Y and Z indicate suitable coefficients.)

As will be understood from the above reactions, the portion of the detecting element 12 on which the catalyst layer 15 is carried exhibits high sensitivity to a partial pressure of oxygen in contact therewith, and thus exhibits an abrupt electric resistance variation when the partial pressure of oxygen is varied. This portion of the detecting element 12 also exhibits electric resistance variation in dependence upon the temperature of the exhaust gases. On the other hand, the portion of the detecting element 12 on which the catalyst layer 15 is not carried is not substantially subjected to catalytic action by the catalyst layer 15. Therefore, the latter portion does not exhibit substantial variations in electric resistance values when the gaseous components are in contact therewith, but instead exhibits electric resistance variation depending mainly upon the temperature of the exhaust gases.

The electric resistance variation (more precisely a voltage established by the electric resistance) which depends upon both the gaseous components and the exhaust gas temperature is detected at the electrodes 13a and 13c, while the electric resistance variation depending mainly upon the exhaust gas temperature is sensed between the electrode 13b and either one of the electrodes 13a and 13c. It should be noted that the value of the electric resistance variation present at the electrodes 13a and 13c and established by the exhaust gas temperature variation is substantially identical with the value of the electric resistance variation which may be sensed between the electrode 13b and either one of the electrodes 13a and 13c and which also has resulted from the exhaust gas temperature variation.

Figure 6:
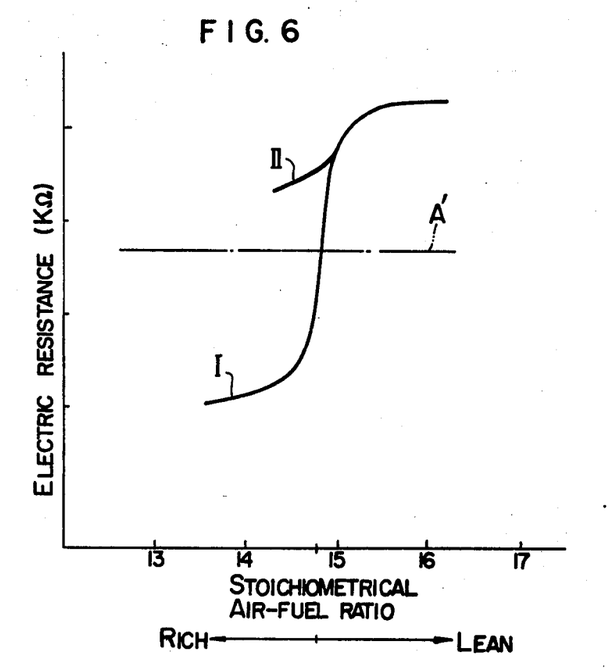
FIG. 6 graphically illustrates a relationship between the air-fuel ratio of an air-fuel mixture and electric resistances detected at different pairs of electrodes of the gas detection apparatus.

FIG. 6 graphically shows a relationship between the air-fuel ratio of the air-fuel mixture and the electric resistances sensed at the different pairs of electrodes. In FIG. 6, curve I shows the relationship between the air-fuel ratio and electric resistance variations resulting from both the exhaust gas temperature and the gaseous components, which were the electrodes 13a and 13c, while a curve II shows the relationship between the air-fuel ratio and electric resistance variations dependent mainly upon the exhaust gas temperature, which were sensed between electrodes 13a and 13b, or between electrodes 13b and 13c. These curves I and II were obtained by an experiment in which the detecting element 12 and the catalyst layer 15 were composed of titanium oxide ($TiO_2$) and platinum (Pt), respectively. Additionally, the exhaust gas was at a temperature of 350° C. In the FIG. 6 graph, the ordinate indicates electric resistance (KΩ) in a logarithm scale, while the obcissa indicates the air-fuel ratio of the exhaust gas with an equally divided scale. As described, the value of the electric resistance variation detected at the electrodes 13a and 13c and dependent on the exhaust gas temperature variation is substantially identical with the value of the electric resistance variation dependent on exhaust gas temperature variation sensed between the electrode 13b and either one of the electrodes 13a and 13c. Therefore, characteristic curves similar to the curves I and II of FIG. 6 can be obtained at different exhaust gas temperatures.

Figure 7:
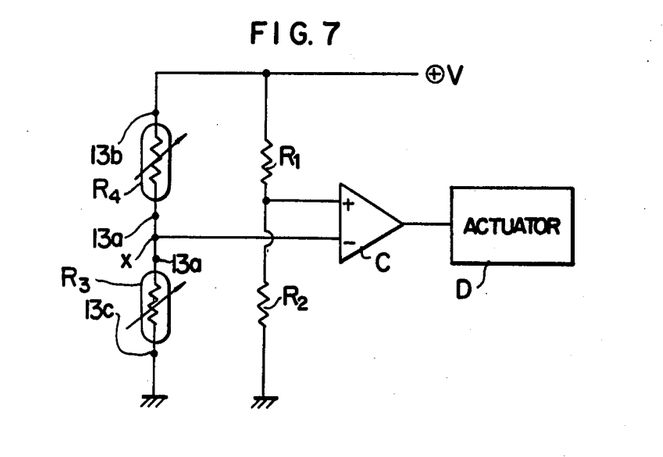
FIG. 7 is a schematic diagram of one example of an electric circuit for determining and controlling the air-fuel ratio utilizing the detection apparatus according to the invention.

FIG. 7 shows an example of an electric circuit incorporating the gas component detection apparatus of the invention. In this circuit, the portion of the detecting element 12 carrying the catalyst layer 15 is represented by a detector resistor $R_3$ between the electrodes 13a and 13c, while the portion of the detecting element 12 not carrying the catalyst layer 15 is represented by another detector resistor $R_4$ between the electrodes 13a and 13b. The detector resistors $R_3$ and $R_4$ are connected in series, and an intermediate point x is connected to an inverted input terminal (−) of a differential operational amplifier C. Reference resistors $R_1$ and $R_2$ are connected in series, and a reference voltage established by these reference resistors is adapted to be applied to the non-inverted other input terminal (+) of the amplifier C. At the intermediate point x, the electric resistance variation sensed across electrodes 13a and 13b due to the temperature variation of the exhaust gas is substantially offset or cancelled by the electric resistance variation across the electrodes 13a and 13c due to this exhaust gas temperature variation. Consequently, there is established at the intermediate portion x a voltage representing only the abrupt electric resistance variation produced by the gaseous components. In other words, the voltage obtained at the intermediate portion x substantially depends upon the concentrations of the gaseous components or the air-fuel ratio.

The electric resistance value of the detecting element 12 will exhibit an abrupt variation when the actual or detected air-fuel ratio is changed from the stoichiometrical air-fuel ratio. Thus, in order to control the actual air-fuel ratio to the stoichiometrical air-fuel ratio, the reference voltage set by the reference resistors to represent the stoichiometrical air-fuel ratio (such reference voltage being indicated by a phantom line A' in FIG. 6 in terms of electric resistance) is applied to the non-inverted input terminal (+) of the amplifier C. The amplifier C compares the voltages applied to both its input terminals, and issues a corresponding output signal for operating an actuator D comprising for example an air-fuel ratio compensation unit of a carburetor. In the case where the detected air-fuel ratio is larger than the stoichiometrical air-fuel ratio whereby the voltage at the intermediate point x is larger than the reference voltage representing the stoichiometrical air-fuel ratio, the amplifier C issues an output signal for operating the actuator D to make the air-fuel ratio smaller, thereby reducing it to the stoichiometrical one. On the other hand, in the case where the detected air-fuel ratio is smaller than the stoichiometrical one and the voltage at the intermediate point x is smaller than the reference voltage, the output signal issued from the amplifier C operates the actuator D to make the air-fuel ratio larger so as to increase it to the stoichiometrical one. In FIG. 7, a character V designates an electric source such as battery.

As will be understood from the foregoing, with the structure of detection apparatus according to the invention, the electric resistance variation exhibited at the portion of the detecting element 12 carrying the catalyst layer 15 and that exhibited at the portion thereof not carrying the catalyst layer 15 can be detected separately. Thus, it becomes possible to offset the electric resistance variation exhibited at the former portion, due to the exhaust gas temperature variation, by the electric resistance variation exhibited at the latter portion. Consequently, the determination of the actual air-fuel ratio, i.e., the determination as to whether or not the actual air-fuel ratio is larger or smaller than the stoichiometrical air-fuel ratio, can be constantly made.

Furthermore, since oxidizing reactions of the gaseous components resulting from catalytic action of the catalyst layer 15 produce a reaction heat, a temperature rise occurs at the surface of the detecting element 12. Therefore, the detecting element 12 exhibits high sensitivity even when the exhaust gas temperature is low, as is the case where the internal combustion engine is started at a low temperature condition.

Figure 8:
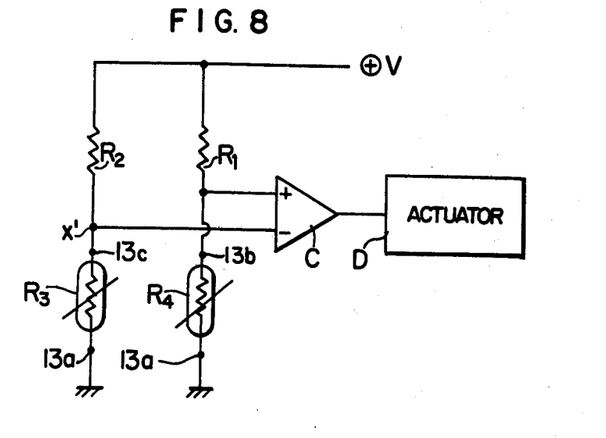
FIG. 8 is a schematic diagram similar to FIG. 7, showing another example of an electric circuit.

It will be understood that the electric circuit shown in FIG. 7 is only one example of a circuit which may be employed. Another electric circuit such as that shown in FIG. 8, also may be used. In the circuit of FIG. 8, the reference resistor $R_2$ and the detector resistor $R_3$ are connected in series, while the reference resistor $R_1$ and the detector resistor $R_4$ also are connected in series. The voltage established at the intermediate point X' between the reference resistor $R_2$ and the detector resistor $R_3$ is applied to the inverted input terminal (−) of the amplifier C, while the voltage established between the reference resistor $R_1$ and the detector resistor $R_4$ is applied to the non-inverted input terminal (+) of C. The remaining structure of this circuit is substantially similar to the electric circuit of FIG. 7. Accordingly, the same or similar parts are indicated by corresponding reference numerals and characters in these figures.

Figure 9A:
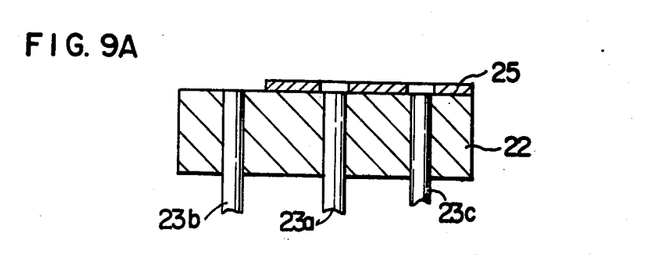
FIG. 9A is a sectional view similar to FIG. 3, showing an essential part of a second embodiment of the detection apparatus according to the invention.
Figure 9B:
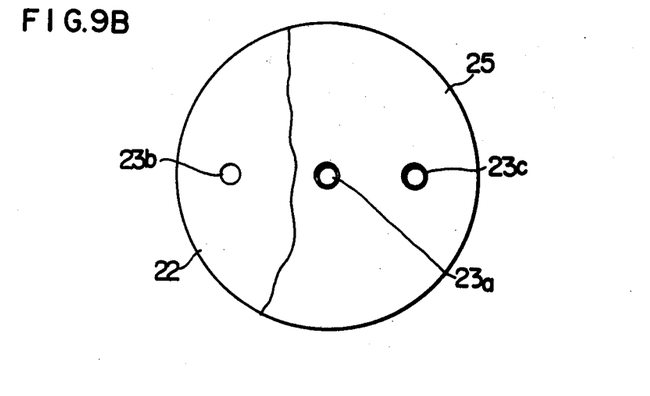
FIG. 9B is a plan view of the part of the detection apparatus shown in FIG. 9A.

FIGS. 9A and 9B illustrate an essential part of a second embodiment of a gas component detection apparatus in accordance with the invention. The second embodiment is substantially similar to the first embodiment. In the second embodiment, however, a catalyst layer 25 is carried on part of the surface of a gas component detecting element 22. The electrodes 23a and 23c are inserted into the detecting element 22 with their outer ends exposed to that portion of the detecting element 22 which carries the catalyst layer 25, while the electrode 23b is inserted into detecting element 22 with its outer end exposed to that portion of element 22 which does not carry the catalyst layer 25. The second embodiment provides an advantage that the expensive catalyst layer 25 can be efficiently utilized. As in to the first embodiment, the detecting element 22 is conposed of a sintered mass of transition metal oxides.

Figure 10:
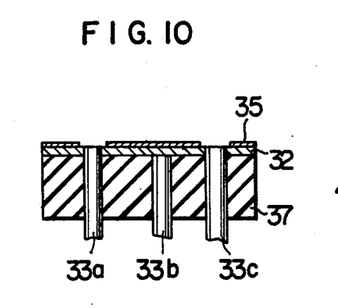
FIG. 10 is a sectional view similar to FIG. 3, showing an essential part of a gas component detection apparatus according to the invention.

FIG. 10 shows an essential part of a third embodiment of a gas detection apparatus in accordance with the invention. In the third embodiment, a gas component detecting element 32 is composed of a thin film composed of semiconductive metal oxides, and the detecting element 32 is retaind on an upper surface of a carrier 37 made of electrically insulative ceramic materials. The detecting element 32 is retained thereon as a thin film, having a thickness of about 100 angstroms to 10 microns, by means such as vacuum evaporation and electric beam evaporation. A catalyst layer 35 is applied to the surface of the detecting element 32 by means such as vacuum evaporation. In FIG. 10, the numerals 33a, 33b and 33c indicate electrodes.

Figure 11:
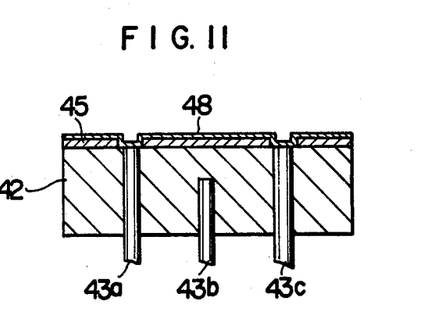
FIGS. 11 to 13 are sectional views similar to FIG. 3, illustrating essential parts of modifications of the first, second and third embodiments, respectively.
Figure 12:
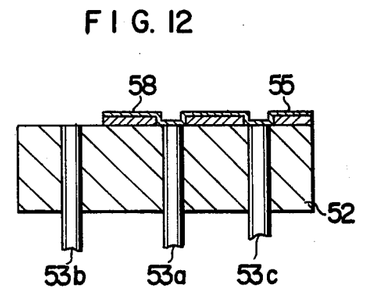
Figure 13:
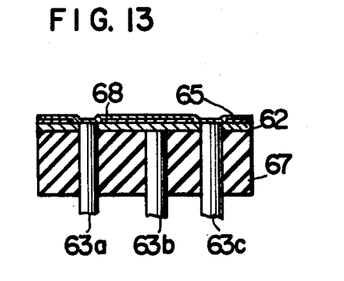

FIGS. 11 to 13 show the essential parts of modifications of the first, second and third embodiments, respectively. In these modifications, the surfaces of gas component detecting elements 42, 52 and 62 with catalyst layers 45, 55 and 65 carried thereon are covered with gas permeable and electrically insulative porous ceramic films 48, 58 and 68, respectively. The ceramic films 48, 58 and 68 are composed, for example, of γ-alumina and are effective to prevent impurities such as phosphor and plumbum contained in the exhaust gases, from attaching to the surfaces of the detecting elements 42, 52 and 62, respectively. In these Figures, numerals 43a, 43b and 43c; 53a, 53b and 53c; and 63a 63b and 63c indicate respectively three electrodes. Furthermore, in FIG. 13, numeral 67 indicates a carrier similar to the carrier 37 of FIG. 10.

It will be understood that the gas component detection apparatus of the present invention can be used not only with internal combustion engines, such as gasoline engine, but also with other combustion devices such as a LP gas engine.

As described above, the gas component detection apparatus of the present invention can determine with high accuracy the air-fuel ratio of the air-fuel mixture, thus enabling precise control of the air-fuel ratio of the air-fuel mixture supplied to the combustion devices. Furthermore, with the structure according to the invention, compensation for a temperature caused electric resistance variation exhibited and detected at one portion of the gas component detecting element can be effected by sensing a corresponding electric resistance variation from another portion thereof. Consequently, temperature compensation can be effected with high accuracy and low cost, as compared with the case where the temperature compensation is achieved by the use of additional means such as thermocouples and thermisters.

What is claimed is:

1. A gas component detection apparatus for detecting gaseous components of exhaust gases from an internal combustion engine and determining whether an air-fuel ratio of an air-fuel mixture supplied thereto is larger or smaller than the stoichiometrical air-fuel ratio comprising:

a gas component detecting element comprising a sintered mass of semiconductive metal oxides, said detecting element having a surface partially exposed to exhaust gases and exhibiting variable electric resistances according to gaseous components and temperatures of the exhaust gases;

a catalyst carried on that surface of said detecting element partially exposed to the exhaust gases for promoting oxidation reactions of the gaseous components of the exhaust gases;

a pair of electrodes inserted into said detecting element in a manner not short-circuited through said catalyst and having outer ends disposed adjacent said catalyst, said electrodes sensing an abrupt change in electric resistances exhibited at that portion of said detecting element near said catalyst resulting from the gaseous components and temperatures of the exhaust gases; and an additional electrode disposed in said detecting element in a relation spaced from said catalyst, said additional electrode detecting, in association with one of said pair of electrodes, a change in electric resistances resulting mainly from the temperatures of the exhaust gases exhibited at that portion of said detecting element substantially spaced from said catalyst.

2. A gas component detection apparatus for detecting gaseous components of exhaust gases from a combustion device comprising:

a gas component detecting element comprising semiconductive metal oxides, said detecting element having a surface partially exposed to exhaust gases from a combustion device and exhibiting variable electric resistances according to the gaseous components and temperatures of the exhaust gases;

a catalyst carried on a larger part of that surface of said detecting element partially exposed to the exhaust gases for promoting oxidation reactions of the gaseous components of the exhaust gases;

a pair of electrodes inserted into said detecting element in a manner not short-circuited through said catalyst and having outer ends disposed adjacent said catalyst, said electrodes sensing an abrupt change in electric resistances exhibited at that portion of said detecting element near said catalyst resulting from the gaseous components and temperatures of the exhaust gases; and an additional electrode disposed in said detecting element in a relation spaced from said catalyst, said additional electrode detecting, in association with one of said pair of electrodes, a change in electric resistances resulting mainly from the temperatures of the exhaust gases exhibited at that portion of said detecting element substantially spaced from said catalyst.

3. A gas component detection apparatus as defined in claim 2, further comprising an electrically-insulative porous ceramic film covering said catalyst.

4. A gas component detection apparatus as defined in claim 2, wherein said detecting element is composed of transition metal oxides.

5. A gas component detection apparatus as defined in claim 2, wherein said detecting element is composed of tin oxide.

6. A gas component detection apparatus as defined in claim 2, wherein said detecting element is composed of a sintered mass of metal oxides.

7. A gas component detection apparatus as defined in claim 6, wherein said additional electrode passes through said detecting element and has an outer end located away from that part of said detecting element which carries said catalyst.

8. A gas component detection apparatus as defined in claim 2, wherein said detecting element is composed of a thin film of metal oxides which is retained on an electrically insulative ceramic carrier.

9. A gas component detection apparatus for detecting gaseous components of exhaust gases from an internal combustion engine and determining whether an air-fuel ratio of an air-fuel mixture supplied thereinto is larger or smaller than the stoichiometrical air-fuel ratio comprising:

gas component detecting means made of metal oxides for exhibiting variable electrical resistances according to gaseous components and temperatures of the exhaust gases;

a catalyst held by said detecting means for promoting oxidation reactions of the gaseous components of the exhaust gases;

a pair of electrodes inserted into said detecting means in such a manner that said catalyst is disposed between said pair of electrodes but does not short-circuit said electrodes and so that substantial oxidation reactions are promoted between said electrodes whereby said electrodes sense an abrupt change in electrical resistances exhibited at a portion of said detecting means near said catalyst resulting from the gaseous components and temperatures of the exhaust gases; and a third electrode disposed in said detecting means in a relation spaced from said catalyst, said third electrode detecting, in association with one of said pair of electrodes, a change in electrical resistance resulting substantially from only the temperature of the exhaust gases exhibited at a portion of said detecting means substantially spaced from said catalyst.

* * * * *